United States Patent
Augier et al.

(10) Patent No.: US 11,786,878 B2
(45) Date of Patent: Oct. 17, 2023

(54) OLIGOMERIZATION PROCESS USING A RECYCLE OF GASEOUS HEADSPACE

(71) Applicant: IFP Energies nouvelles, Rueil-Malmaison (FR)

(72) Inventors: Frédéric Augier, Rueil-Malmaison (FR); Alexandre Vonner, Rueil-Malmaison (FR); Pedro Maximiano Raimundo, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 74 days.

(21) Appl. No.: 17/631,205

(22) PCT Filed: Jul. 20, 2020

(86) PCT No.: PCT/EP2020/070438
§ 371 (c)(1),
(2) Date: Jan. 28, 2022

(87) PCT Pub. No.: WO2021/018651
PCT Pub. Date: Feb. 4, 2021

(65) Prior Publication Data
US 2022/0258117 A1 Aug. 18, 2022

(30) Foreign Application Priority Data
Jul. 31, 2019 (FR) ...................................... 1908755

(51) Int. Cl.
*B01J 10/00* (2006.01)
*B01J 4/00* (2006.01)
*B01J 19/24* (2006.01)
*C07C 2/32* (2006.01)

(52) U.S. Cl.
CPC ............. *B01J 10/002* (2013.01); *B01J 4/004* (2013.01); *B01J 19/2465* (2013.01); *C07C 2/32* (2013.01)

(58) Field of Classification Search
CPC ........ C07C 11/107; C07C 2/32; B01J 10/002; B01J 4/004; B01J 19/2465
See application file for complete search history.

(56) References Cited

U.S. PATENT DOCUMENTS

| | | | |
|---|---|---|---|
| 10,399,912 B2 * | 9/2019 | Han | C08F 6/10 |
| 10,626,063 B2 | 4/2020 | Azam et al. | |
| 11,207,657 B2 | 12/2021 | Augier et al. | |

(Continued)

FOREIGN PATENT DOCUMENTS

| | | |
|---|---|---|
| WO | 2016009360 A1 | 1/2016 |
| WO | 2019011806 A1 | 1/2019 |

OTHER PUBLICATIONS

International Search Report for PCT/EP2020/070438 dated Oct. 13, 2020.

*Primary Examiner* — Ali Z Fadhel
(74) *Attorney, Agent, or Firm* — MILLEN, WHITE, ZELANO AND BRANIGAN, P.C.; Harry B. Shubin

(57) ABSTRACT

The present invention relates to an oligomerization process implemented in a gas/liquid reactor comprising a headspace recycle loop. The process more particularly relates to the oligomerization of ethylene to linear alpha-olefins such as 1-butene, 1-hexene, 1-octene or a mixture of linear alpha-olefins.

15 Claims, 1 Drawing Sheet

(56) References Cited

U.S. PATENT DOCUMENTS

| | | | |
|---|---|---|---|
| 2009/0203947 A1* | 8/2009 | Schneider | C07C 7/09 422/198 |
| 2010/0249343 A1* | 9/2010 | Kleingeld | C07C 2/36 526/348 |
| 2012/0330078 A1* | 12/2012 | Hofmann | C07C 2/08 585/520 |
| 2015/0126790 A1* | 5/2015 | Venter | C07C 2/32 585/511 |
| 2015/0291486 A1* | 10/2015 | Weber | C08F 2/42 585/512 |
| 2015/0299069 A1 | 10/2015 | Azam et al. | |
| 2017/0210680 A1 | 7/2017 | Azam et al. | |
| 2020/0139334 A1* | 5/2020 | Al-Dughaiter | C07C 2/08 |
| 2020/0199039 A1 | 6/2020 | Azam et al. | |
| 2021/0009486 A1* | 1/2021 | Allen | C07C 2/08 |

\* cited by examiner

OLIGOMERIZATION PROCESS USING A RECYCLE OF GASEOUS HEADSPACE

TECHNICAL FIELD

The present invention relates to an oligomerization process implemented in a gas/liquid reactor comprising a headspace recycle loop. The process more particularly relates to the oligomerization of ethylene to linear alpha-olefins such as 1-butene, 1-hexene, 1-octene or a mixture of linear alpha-olefins.

PRIOR ART

The invention relates to the field of oligomerization processes employing gas/liquid reactors, which are also called bubble columns. Owing to the exothermic nature of oligomerization reactions, bubble columns likewise comprise a recirculation loop whereby a liquid fraction is withdrawn, cooled and reintroduced into the reaction chamber. Said recirculation loop enables high homogeneity of the concentrations and control of the temperature throughout the reaction volume, owing to the high heat transfer capacity associated with the recirculation loop.

One disadvantage encountered in oligomerization processes when using this type of column is the management of the gas phase, also known as the headspace. The reason is that said headspace comprises gaseous components of low solubility in the liquid phase, compounds which are partially soluble in the liquid but are inert, and gaseous ethylene not dissolved in said liquid. The passage of gaseous ethylene from the liquid phase toward the gas phase (or headspace) is a phenomenon referred to as breakthrough. The headspace is purged in order to remove said gaseous compounds. When the amount of gaseous ethylene present in the headspace is substantial, the purging of the headspace leads to a significant loss of ethylene, which is detrimental to the productivity and to the cost of the oligomerization process.

To improve the efficiency of the oligomerization process in terms of productivity and cost, it is therefore vital to limit the loss of unreacted ethylene contained in the headspace so as to improve its conversion in said process, while retaining a high selectivity for desired linear alpha-olefins.

The prior art processes employing a recirculation loop, as illustrated in FIG. 1, do not make it possible to limit the loss of gaseous ethylene, and the purging of the headspace results in an exit of gaseous ethylene from the reactor that is adverse for the yield and the cost of the process.

In patent applications WO2019/011806 and WO2019/011609, the applicant has described processes enabling an increase in the contact surface area between the upper part of the liquid fraction and the headspace, by way of a dispersion means or vortex, so as to promote the passage of the ethylene contained in the headspace toward the liquid phase at the liquid/gas interface. These processes, however, are insufficient when the amount of ethylene in the headspace is substantial because of a high level of breakthrough.

In the course of the research, moreover, the applicant has found that in a reactor operating with a constant injection rate of gaseous ethylene, the amount of dissolved ethylene and therefore the level of breakthrough are dependent on the dimensions of the reactors implementing the process, and notably on the height of the liquid phase. Indeed, the lower the height, the shorter the time during which the gaseous ethylene reaches the liquid phase for dissolution, and the higher the level of breakthrough.

The applicant has surprisingly found a new process, employing a step of recycling of the headspace into the lower part of the liquid phase, which enables an optimization of the dissolution of the gaseous ethylene introduced into the process, and regulation of the pressure within the reactor, without consequent loss of ethylene and irrespective of the dimensions of the reactor employed. More particularly, the process allows the selective production of linear alpha-olefins such as 1-butene, 1-hexene and 1-octene.

Another advantage of the recycling step according to the invention is that it enables simple and economic compensation of the phenomenon of breakthrough of the gaseous ethylene into the headspace in an oligomerization process, irrespective of the dimensions of the reactor.

BRIEF DESCRIPTION OF THE INVENTION

The present invention relates to an oligomerization process implemented in a gas/liquid reactor at a pressure of between 0.1 and 10.0 MPa, at a temperature of between 30 and 200° C., comprising the following steps:
   a) a step of introducing a catalytic oligomerization system comprising a metal catalyst and an activating agent into a reaction chamber comprising a liquid phase in a lower zone and a gas phase in an upper zone,
   b) a step of contacting said catalytic system with gaseous ethylene by introducing said ethylene into the lower zone of the reaction chamber,
   c) a step of withdrawing a liquid fraction,
   d) a step of cooling the fraction withdrawn in step c) by passing said fraction into a heat exchanger,
   e) a step of introducing the fraction cooled in step d) into the upper part of the lower zone of the reaction chamber,
   f) a step of recycling a gaseous fraction, withdrawn from the upper zone of the reaction chamber and introduced at the lower part of the reaction chamber, into the liquid fraction.

Preferably, the liquid phase in the lower zone of the reaction chamber has a degree of saturation in dissolved ethylene of more than 70.0%.

Preferably, the gas phase withdrawn in step f) is introduced as a mixture with the gaseous ethylene introduced in step b).

Preferably, the rate of withdrawal of the gaseous fraction in step f) is between 0.1 and 100% of the flow rate of gaseous ethylene introduced in step b).

Preferably, the gaseous fraction withdrawn in step f) is introduced in the lateral lower part of the reaction chamber.

Preferably, the rate of withdrawal of the gaseous fraction in step f) is dependent on the pressure within the reaction chamber.

Preferably, a second gaseous purge stream is withdrawn from the gas phase.

Preferably, the flow rate of the second gaseous stream is between 0.005 and 1.00% of the flow rate of ethylene introduced in step b).

Preferably, a stream of gaseous hydrogen is introduced in step b) into the reaction chamber, with a flow rate representing 0.2 to 1.0% by mass of the flow rate of incoming ethylene.

Preferably, the concentration of catalyst in the catalytic system is between 0.1 and 50.0 ppm by mass of atomic metal relative to the reaction mass.

Preferably, the catalytic oligomerization reaction is implemented continuously.

Preferably, the linear olefins obtained comprise from 4 to 20 carbon atoms.

The invention likewise relates to a device for implementing the ethylene oligomerization process described above, comprising:
- a reaction chamber i), of elongate shape along the vertical axis, comprising
  a liquid phase located in a lower zone and comprising, preferably consisting of, reaction products, gaseous and dissolved ethylene, a catalytic system and an optional solvent, and a gas phase located in an upper zone above the lower zone and comprising gaseous ethylene and also incondensable gases (methane notably),
- a means ii) for introducing gaseous ethylene, located in the lateral lower part of said reaction chamber, employing a means for distributing the gaseous ethylene within said liquid phase of the reaction chamber,
- a means iii) for introducing the catalytic system, comprising a metal catalyst, at least one activator and at least one additive, said means being located in the lower part of the reaction chamber,
- a recirculation loop iv) comprising a withdrawing means at the base (preferably at the bottom) of the reaction chamber for withdrawing a liquid fraction toward a heat exchanger enabling the cooling of said liquid, and a means for introducing said cooled liquid, said introduction being carried out into the liquid phase in the upper part of the lower zone of the reaction chamber,
- a recycle loop v) for the headspace into the lower zone of the liquid phase, comprising a means for withdrawing a gaseous fraction at the gas phase of the reaction chamber and a means for introducing said withdrawn gaseous fraction into the liquid phase in the lower zone of the reaction chamber.

Preferably, in said device, the gaseous fraction withdrawn is introduced by way of the means ii) for introducing gaseous ethylene.

Preferably, in said device, the gaseous fraction withdrawn in the recycle loop v) is introduced by way of a gas distributor.

Definitions & Abbreviations

Throughout the description, the terms or abbreviations below have the following meanings:

Oligomerization is understood to mean any addition reaction of a first olefin with a second olefin, identical to or different from the first olefin. The olefin thus obtained has the empirical formula $C_nH_{2n}$, where n is equal to or greater than 4.

Alpha-olefin is understood to mean an olefin in which the double bond is located at the terminal position of the alkyl chain.

Catalytic system is understood to mean the mixture of at least one metal catalyst and of at least one activating agent, in the presence optionally of at least one additive and optionally in the presence of at least one solvent.

Liquid phase is understood to mean the mixture of all of the compounds which are in a liquid physical state under the temperature and pressure conditions of the reaction chamber.

Gas phase, also referred to as headspace, is understood to mean the mixture of all of the compounds which are in the gaseous physical state under the temperature and pressure conditions of the reaction chamber: in the form of bubbles present in the liquid, and also in the top part of the reactor (headspace of the reactor).

Lower zone of the reaction chamber is understood to mean the part of the chamber that comprises the liquid phase, gaseous ethylene, products of the reaction such as the desired linear alpha-olefin (i.e. but-1-ene, hex-1-ene, oct-1-ene), and the catalytic system.

Upper zone of the reaction chamber is understood to mean the part of the chamber that is located at the apex of the chamber, in other words directly above the lower zone and consisting of the headspace.

Lateral lower part of the reaction chamber is understood to mean a part of the shell of the reactor located in the bottom part and on the side.

Incondensable gas is understood to mean an entity in gaseous physical form which only partially dissolves in the liquid at the temperature and pressure conditions of the reaction chamber and which can, under certain conditions, accumulate in the headspace of the reactor (example here: ethane).

Understood by t/h is the value of a rate expressed in tonnes per hour, and by kg/s the value of a flow rate in kilograms per second.

The terms reactor or device denote all of the means which enable the implementation of the oligomerization process according to the invention, such as in particular the reaction chamber and the recirculation loop.

The lower part preferably denotes the lower quarter of the reaction chamber.

Fresh gaseous ethylene is understood to mean the ethylene external to the process that is introduced in step b) via the means ii) of the process according to the invention.

DETAILED DESCRIPTION OF THE INVENTION

It is specified that, throughout this description, the expression "between . . . and . . . " should be understood as including the limits mentioned.

Within the meaning of the present invention, the various embodiments presented can be used alone or in combination with one another, without any limit to the combinations.

The present invention relates to an oligomerization process implemented in a gas/liquid reactor at a pressure of between 0.1 and 10.0 MPa, at a temperature of between 30 and 200° C., comprising the following steps:
- a) a step of introducing a catalytic oligomerization system comprising a metal catalyst and an activating agent into a reaction chamber comprising a liquid phase in a lower zone and a gas phase in an upper zone,
- b) a step of contacting said catalytic system with gaseous ethylene by introducing said ethylene into the lower zone of the reaction chamber,
- c) a step of withdrawing a liquid fraction,
- d) a step of cooling the fraction withdrawn in step c) by passing said fraction into a heat exchanger,
- e) a step of introducing the fraction cooled in step d) into the upper part of the lower zone of the reaction chamber,
- f) a step of recycling a gaseous fraction, withdrawn from the upper zone of the reaction chamber and introduced at the lower part of the reaction chamber, into the liquid fraction.

Preferably, in a gas/liquid reactor, the flow rate of gaseous ethylene introduced in step b) is dependent on the pressure in the reaction chamber. In the event of an increase in the pressure in the reactor, therefore, owing to a high level of breakthrough by the ethylene into the gas phase, the flow rate of gaseous ethylene introduced in step b) goes down, leading to a decrease in the amount of ethylene dissolved in the liquid phase, and hence in the ethylene saturation. This decrease is detrimental to the conversion of the ethylene and is accompanied by a decrease in the productivity of the reactor, and possibly in its selectivity.

The process according to the invention advantageously has a degree of saturation of dissolved ethylene in the liquid phase of more than 70.0%, preferably between 70.0 and 100%, preferably between 80.0 and 100%, preferentially between 80.0 and 99.0%, preferably between 85.0 and 99.0% and more preferably still between 90.0 and 98.0%.

The degree of saturation of dissolved ethylene may be measured by any method known to a person skilled in the art and, for example, by gas-chromatographic (commonly referred to as GC) analysis of a fraction of the liquid phase withdrawn from the reaction chamber.

Another advantage of the recycling step according to the invention is that it enables simple and economic compensation for the phenomenon of breakthrough of the gaseous ethylene into the headspace in an oligomerization process, irrespective of the dimensions of the reactor.

Oligomerization Process

The oligomerization process according to the invention allows linear alpha-olefins to be obtained by the contacting of ethylene and a catalytic system, optionally in the presence of a solvent.

Any catalytic system known to a person skilled in the art and capable of being employed in the dimerization, trimerization or tetramerization processes and more generally in the oligomerization processes according to the invention comes within the field of the invention. Said catalytic systems and also the implementations thereof are described in particular in patent applications FR 2 984 311, FR 2 552 079, FR 3 019 064, FR 3 023 183, FR 3 042 989 or else in application FR 3 045 414.

Preferably, the catalytic systems comprise, preferably consist of:
a metal precursor, preferably based on nickel, on titanium or on chromium,
an activating agent,
optionally an additive, and
optionally a solvent.

The Metal Precursor

The metal precursor used in the catalytic system is chosen from compounds based on nickel, on titanium or on chromium.

In one embodiment, the metal precursor is based on nickel and preferably comprises nickel with a (+II) oxidation state. Preferably, the nickel precursor is chosen from nickel(II) carboxylates, such as, for example, nickel 2-ethylhexanoate, nickel(II) phenates, nickel(II) naphthanates, nickel(II) acetate, nickel(II) trifluoroacetate, nickel(II) triflate, nickel (II) acetylacetonate, nickel(II) hexafluoroacetylacetonate, π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or nonhydrated form, taken alone or as a mixture.

In a second embodiment, the metal precursor is based on titanium and preferably comprises a titanium aryloxy or alkoxy compound.

The titanium alkoxy compound advantageously corresponds to the general formula [Ti(OR)$_4$] in which R is a linear or branched alkyl radical. Mention may be made, among the preferred alkoxy radicals, as nonlimiting examples, of tetraethoxy, tetraisopropoxy, tetra(n-butoxy) and tetra(2-ethylhexyloxy).

The titanium aryloxy compound advantageously corresponds to the general formula [Ti(OR')$_4$] in which R' is an aryl radical substituted or unsubstituted by alkyl or aryl groups. The R' radical can comprise heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl) phenoxy, 4-methyl-2,6-di(tert-butyl)phenoxy, 2,6-dichloro-4-(tert-butyl)phenoxy and 2,6-dibromo-4-(tert-butyl) phenoxy, the biphenoxy radical, binaphthoxy or 1,8-naphthalenedioxy.

According to a third embodiment, the metal precursor is based on chromium and preferably comprises a chromium (II) salt, a chromium(III) salt or a salt with a different oxidation state which can comprise one or more identical or different anions, such as, for example, halides, carboxylates, acetylacetonates or alkoxy or aryloxy anions. Preferably, the chromium-based precursor is chosen from CrCl$_3$, CrCl$_3$ (tetrahydrofuran)$_3$, Cr(acetylacetonate)$_3$, Cr(naphthenate)$_3$, Cr(2-ethylhexanoate)$_3$ or Cr(acetate)$_3$.

The concentration of nickel, of titanium or of chromium is between 0.01 and 300.0 ppm by weight of atomic metal, with respect to the reaction mass, preferably between 0.02 and 100.0 ppm, preferentially between 0.03 and 50.0 ppm, more preferentially between 0.5 and 20.0 ppm and more preferentially still between 2.0 and 50.0 ppm by weight of atomic metal, with respect to the reaction mass.

The Activating Agent

Whatever the metal precursor, the catalytic system additionally comprises one or more activating agents chosen from aluminium-based compounds, such as methylaluminium dichloride (MeAlCl$_2$), dichloroethylaluminum (EtAlCl$_2$), ethylaluminium sesquichloride (Et$_3$Al$_2$Cl$_3$), chlorodiethylaluminum (Et$_2$AlCl), chlorodiisobutylaluminium (i-Bu$_2$AlCl), triethylaluminium (AlEt$_3$), tripropylaluminium (Al(n-Pr)$_3$), triisobutylaluminum (Al(i-Bu)$_3$), diethylethoxyaluminium (Et$_2$AlOEt), methylaluminoxane (MAO), ethylaluminoxane and modified methylaluminoxanes (MMAO).

The Additive

Optionally, the catalytic system comprises one or more additives.

When the catalytic system is based on nickel, the additive is chosen from:
compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or compounds of phosphine type independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite, or compounds corresponding to the general formula (I) or one of the tautomers of said compound:

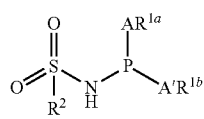

(I)

in which:
A and A', which are identical or different, are independently an oxygen or a single bond between the phosphorus atom and a carbon atom,
the $R^{1a}$ and $R^{1b}$ groups are independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-di(trifluoromethyl)phenyl, benzyl, naphthyl, bisnaphthyl, pyridyl, bisphenyl, furanyl or thiophenyl groups,
the $R^2$ group is independently chosen from the methyl, trifluoromethyl, ethyl, n-propyl, isopropyl, n-butyl, isobutyl, t-butyl, pentyl, cyclohexyl or adamantyl groups, which are substituted or unsubstituted and contain or do not contain heteroelements; the phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl or thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-di(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, di(2-methoxyethyl) ether, benzofuran, glyme and diglyme, taken alone or as a mixture.

When compounds the catalytic system is based on chromium, the additive is chosen from:
of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or aryloxy compounds of general formula $[M(R^3O)_{2-n} X_n]_y$, in which:
M is chosen from magnesium, calcium, strontium and barium, preferably magnesium,
$R^3$ is an aryl radical containing from 6 to 30 carbon atoms and X is a halogen or an alkyl radical containing from 1 to 20 carbon atoms,
n is an integer which can take the values of 0 or 1, and
y is an integer between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals can be carried by one and the same molecule, such as, for example, the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

The Solvent

In another embodiment according to the invention, the catalytic system optionally comprises one or more solvents.

The solvent is chosen from the group formed by aliphatic and cycloaliphatic hydrocarbons, such as hexane, cyclohexane, heptane, butane or isobutane.

Preferably, the solvent used is cyclohexane.

In one embodiment, a solvent or a mixture of solvents may be used during the oligomerization reaction. Said solvent is advantageously chosen independently from the group formed by aliphatic and cycloaliphatic hydrocarbons, such as hexane, cyclohexane, heptane, butane or isobutane.

Preferably, the linear alpha-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear alpha-olefins chosen from but-1-ene, hex-1-ene or oct-1-ene.

Advantageously, the oligomerization process is implemented at a pressure of between 0.1 and 10.0 MPa, preferably between 0.2 and 9.0 MPa and preferentially between 0.3 and 8.0 MPa, at a temperature of between 30 and 200° C., preferably between 35 and 150° C. and preferentially between 45 and 140° C.

The concentration of catalyst in the catalytic system is preferably between 0.1 and 50.0 ppm by mass of atomic metal relative to the reaction mass, preferably between 0.4 and 30.0 ppm, preferably between 0.6 and 20.0 ppm, preferably between 0.8 and 10.0 ppm and preferably between 1.0 and 6.0 ppm by mass of atomic metal relative to the reaction mass.

According to one embodiment, the oligomerization process is implemented batchwise. The catalytic system, constituted as described above, is introduced into a reactor provided with the usual stirring, heating and cooling devices, then pressurization with ethylene is carried out to the desired pressure, and the temperature is adjusted to the desired value. The oligomerization device is maintained at a constant pressure by introduction of gaseous ethylene until the total volume of liquid produced represents, for example, from 2 to 50 times the volume of the catalytic solution introduced beforehand. The catalyst is then destroyed by any usual means known to a person skilled in the art and then the products of the reaction and the solvent are withdrawn and separated.

According to another embodiment, the oligomerization process is implemented continuously. The catalytic system, constituted as described above, is injected at the same time as the ethylene into a reactor stirred by conventional mechanical means known to a person skilled in the art or by external recirculation, and maintained at the desired temperature. The components of the catalytic system can also be injected separately into the reaction medium. The gaseous ethylene is introduced by an intake valve in dependence on the pressure, which keeps the latter constant in the reactor. The reaction mixture is withdrawn by means of a valve in dependence on the liquid level, so as to keep the latter constant. The catalyst is destroyed continuously by any usual means known to a person skilled in the art and then the products resulting from the reaction, and also the solvent, are separated, for example by distillation. The ethylene which has not been converted can be recycled in the reactor. The catalyst residues included in a heavy fraction can be incinerated.

Step a) of Introducing the Catalytic System

The process according to the invention comprises a step a) of introducing a catalytic system comprising a metal catalyst and an activating agent, and optionally of introducing a solvent or a mixture of solvents, into a reaction chamber comprising a liquid phase in a lower zone and a gas phase in an upper zone.

Preferably, the catalytic system is introduced into the liquid phase in the lower part of the reaction chamber and preferably in the bottom of the reaction chamber.

Preferably, the pressure for introduction into the reaction chamber is between 0.1 and 10.0 MPa, preferably between 0.2 and 9.0 MPa and preferentially between 0.3 and 8.0 MPa.

Preferably, the temperature for introduction into the reaction chamber is between 30 and 200° C., preferably between 35° C. and 150° C. and preferentially between 45° C. and 140° C.

Step b) of Contacting with Gaseous Ethylene

The process according to the invention comprises a step b) of contacting the catalytic system introduced in step a) with the gaseous ethylene. Said gaseous ethylene is introduced into the liquid phase at the lower part of the reaction chamber, preferably on the lateral lower part of the reaction chamber. The gaseous ethylene introduced comprises fresh gaseous ethylene, and preferably said fresh gaseous ethylene is combined with gaseous ethylene recycled in a separation step after the oligomerization process.

In the implementation of the process according to the invention, following the step of introducing the gaseous ethylene, the liquid phase comprises undissolved gaseous ethylene and so, according to the zones of the reaction chamber, the liquid phase corresponds to a gas-liquid mixture between, notably, the liquid phase and the gaseous ethylene. Preferably, the zone in the bottom of the reaction chamber beneath the level at which the gaseous ethylene is introduced comprises and preferably consists of the liquid phase without gaseous ethylene.

Preferably, the gaseous ethylene is distributed by dispersion during the introduction thereof into the lower liquid phase of the reaction chamber by a means able to carry out said dispersion uniformly over the entire cross section of the reactor. Preferably, the dispersion means is chosen from a distributor network with a homogeneous distribution of the ethylene injection points over the entire cross section of the reactor.

Preferably, the velocity of the gaseous ethylene at the outlet of the orifices is between 1.0 and 30.0 m/s. Its superficial velocity (volumetric gas velocity divided by the cross section of the reaction chamber) is between 0.5 and 10.0 cm/s and preferably between 1.0 and 8.0 cm/s.

Preferably, the gaseous ethylene is introduced at a flow rate of between 1 and 250 t/h, preferably between 3 and 200 t/h, preferably between 5 and 150 t/h and preferably between 10 and 100 t/h.

Preferably, the flow rate of gaseous ethylene introduced in step b) is dependent on the pressure in the reaction chamber.

According to a specific embodiment of the invention, a stream of gaseous hydrogen can also be introduced into the reaction chamber, with a flow rate representing from 0.2% to 1.0% by weight of the flow rate of incoming ethylene. Preferably, the stream of gaseous hydrogen is introduced by the pipe employed for the introduction of the gaseous ethylene.

Step c) of Withdrawing a Fraction of the Liquid Phase

The process according to the invention comprises a step c) of withdrawing a fraction of the liquid phase preferably in the lower part of the reaction chamber.

The withdrawal implemented in step c) is preferably carried out in the lower part of the reaction chamber, preferably below the level of injection of gaseous ethylene, and preferably in the bottom of the chamber. The withdrawal is carried out by any means capable of carrying out the withdrawal and preferably by a pump.

Preferably, the withdrawal flow rate is between 500 and 10,000 t/h and preferably between 800 and 7000 t/h.

In one embodiment a second stream is withdrawn from the liquid phase. Said second stream corresponds to the effluent obtained at the end of the oligomerization process, and can be sent to a separating section located downstream of the device employed in the process according to the invention.

According to a preferred embodiment, the liquid fraction withdrawn from the liquid phase is divided into two streams. The first, principal stream is sent to the cooling step d), and the second stream corresponds to the effluent and is sent to the downstream separating section.

Advantageously, the flow rate of said second stream is regulated so as to maintain a constant liquid level in the reactor. Preferably, the flow rate of said second stream is from 5 to 200 times lower than the liquid flow rate sent to the cooling step. Preferably, the flow rate of said effluent is from 5 to 150 times lower, preferably from 10 to 120 times lower and preferentially from 20 to 100 times lower.

Step d) of Cooling the Liquid Fraction

The process according to the invention comprises a step d) of cooling the liquid fraction withdrawn in step c).

Preferably, the cooling step is carried out by the circulation of the main liquid stream withdrawn in step c) through one or more heat exchangers located inside or outside the reaction chamber and preferably outside.

The heat exchanger enables a decrease in the temperature of the liquid fraction of 1.0 to 30.0° C., preferably between 2.0 and 20° C., preferably between 2.0 and 15.0° C., preferably between 2.5 and 10.0° C., preferably from 3.0 to 9.0° C., preferably from 4.0 to 8.0° C. Advantageously, the cooling of the liquid fraction makes it possible to keep the temperature of the reaction medium within the desired temperature ranges.

Advantageously, carrying out the step of cooling the liquid via the recirculation loop also makes it possible to carry out the stirring of the reaction medium and thus to homogenize the concentrations of the reactive entities throughout the liquid volume of the reaction chamber.

Step e) of Introducing the Cooled Liquid Fraction

The process according to the invention comprises a step e) of introducing the liquid fraction cooled in step d).

The introduction of the cooled liquid fraction resulting from step d) is carried out in the gaseous portion of the reaction chamber, preferably at the top of said chamber, by any means known to a person skilled in the art.

Preferably, the flow rate for introduction of the cooled liquid fraction is between 500 and 10,000 t/h and preferably between 800 and 7000 t/h.

wherein steps c) to e) constitute a recirculation loop. Advantageously, the recirculation loop enables the stirring of the reaction medium and thus the homogenization of the concentrations of the reactive entities throughout the liquid volume of the reaction chamber.

Step f) of Recycling a Gaseous Fraction Withdrawn from the Gas Phase

The process according to the invention comprises a step f) of recycling a gaseous fraction, withdrawn from the gas phase in the reaction chamber and introduced at the lower part of the reaction chamber, into the liquid phase, preferably in the lateral lower part of the reaction chamber, preferably at the bottom of the reaction chamber. The lower part denotes the lower quarter of the reaction chamber.

The step f) of recycling the gaseous fraction is also called a recycle loop. The withdrawal of the gaseous fraction, implemented in step f), is carried out by any means suitable for performing the withdrawal, and preferably by a compressor.

One advantage of the recycling step according to the invention is to compensate the phenomenon of breakthrough of ethylene into the headspace. The phenomenon of breakthrough corresponds to the gaseous ethylene which crosses the liquid phase without dissolving and which passes into the headspace. When the flow rate of gaseous ethylene injected and the headspace volume are fixed at a given value, breakthrough then leads to an increase in pressure in the reaction chamber. In a gas/liquid reactor employed according to a preferred process, the flow rate of introduction of the ethylene in step b) is dependent on the pressure in the reaction chamber. Accordingly, in the case of an increase in the pressure in the reactor owing to a high level of breakthrough of the ethylene into the gas phase, the flow rate of gaseous ethylene introduced in step b) decreases, so giving rise to a decrease in the amount of ethylene dissolved in the liquid phase and hence in the saturation. The decrease in saturation is detrimental to the conversion of ethylene and is accompanied by decreasing the productivity of the reactor. The step of recycling a gaseous fraction according to the invention therefore allows the saturation of dissolved ethylene to be optimized and hence the volume productivity of the process to be improved.

The gas phase withdrawn in step f) may be introduced into the reaction chamber alone or as a mixture with the gaseous ethylene introduced in step b). Preferably, the gas phase is introduced as a mixture with the gaseous ethylene introduced in step b).

In one particular embodiment, the gas phase withdrawn in step f) is introduced into the reaction chamber by being dispersed in the lower liquid phase of the reaction chamber by a means capable of carrying out said dispersion uniformly over the entire cross section of the reactor. Preferably, the dispersion means is chosen from a distributor network with a homogeneous distribution of the points of injection of the gas phase withdrawn in step f) over the entire cross section of the reactor.

Preferably, the velocity of the gaseous fraction withdrawn at the outlet of the orifices is between 1.0 and 30.0 m/s. Its superficial velocity (volumetric gas velocity divided by the cross section of the reaction chamber) is between 0.5 and 10.0 cm/s and preferably between 1.0 and 8.0 cm/s.

Preferably, the rate of withdrawal of the fraction is between 0.1 and 100% of the flow rate of gaseous ethylene introduced in step b), preferably 0.5 and 90.0%, preferably 1.0 and 80.0%, preferably between 2.0 and 70.0%, preferably between 4.0 and 60.0%, preferably between 5.0 and 50.0%, preferably between 10.0 and 40.0% and preferentially between 15.0 and 30.0%.

Advantageously, the rate of withdrawal of the gaseous fraction in step f) is dependent on the pressure within the reaction chamber, so making it possible to maintain the pressure at a value or in a desired range and so to compensate the phenomenon of breakthrough of gaseous ethylene into the headspace.

In one particular embodiment, the gaseous fraction withdrawn in step f) is divided into two streams: a first, principal gas stream, which is recycled directly into the reaction chamber, and a second gas stream.

In one preferred embodiment, said second gas stream corresponds to a purge of the headspace, allowing a part of the uncondensable gases to be removed.

Preferably, the flow rate of the second gas stream is between 0.005 and 1.00% of the flow rate of ethylene introduced in step b), preferably between 0.01 and 0.50%.

Oligomerization Reaction Device

Numerous reactors employing a liquid phase and a gas phase consist of a reaction chamber comprising a liquid phase in a lower zone comprising gaseous ethylene, and a gas phase in an upper zone, a loop for recirculating a liquid fraction to a heat exchanger, allowing the liquid fraction to be cooled before it is reinjected into the main chamber. The flow rate in the recirculation loop allows effective homogenization of the concentrations and the control of the temperature in the liquid phase within the reaction chamber.

The reaction device employed by the process according to the invention belongs to the field of gas/liquid reactors such as bubble columns. More particularly, the reaction device according to the invention comprises the following elements:
- a reaction chamber i), of elongate shape along the vertical axis, comprising
  a liquid phase located in a lower zone, comprising and preferably consisting of the products of the reaction, dissolved and gaseous ethylene, a catalytic system and an optional solvent, and a gas phase, located in an upper zone above the lower zone, comprising gaseous ethylene and also uncondensable gases (ethane notably),
- a means ii) for introducing gaseous ethylene, located in the lateral lower part of said reaction chamber, employing a means for distributing the gaseous ethylene within said liquid phase of the reaction chamber,
- a means iii) for introducing the catalytic system, comprising a metal catalyst, at least one activator and at least one additive, said means being located in the lower part of the reaction chamber,
- a recirculation loop iv) comprising a withdrawing means at the base (preferably at the bottom) of the reaction chamber for withdrawing a liquid fraction toward a heat exchanger enabling the cooling of said liquid, and a means for introducing said cooled liquid, said introduction being carried out into the liquid phase in the upper part of the lower zone of the reaction chamber,
- a recycle loop v) for the gas phase into the lower zone of the liquid phase, comprising a means for withdrawing a gaseous fraction at the gas phase of the reaction chamber and a means for introducing said withdrawn gaseous fraction into the liquid phase in the lower zone of the reaction chamber.

i) A Reaction Chamber

According to the invention, any reaction chamber known to a person skilled in the art and capable of carrying out the process according to the invention can be envisaged. Preferably, the reaction chamber is cylindrical in form and has a height to width ratio (denoted H/W) of between 1 and 17, preferably between 1 and 8, preferably between 2 and 7 and preferentially between 2 and 4.

Preferably, the reaction chamber comprises a means for purging the uncondensable gases in the gas phase.

Preferably, the reaction chamber also comprises a pressure sensor, allowing the pressure within the reaction chamber to be controlled and, preferably, to be kept constant. Preferably, in the event of a decrease in the pressure, said pressure is kept constant by the introduction of gaseous ethylene into the reaction chamber.

According to the invention, in the event of the phenomenon of breakthrough of ethylene into the gas phase, said pressure is kept constant by the implementation of the recycle loop v), described below.

Accordingly, the headspace recycle loop makes it possible, advantageously, in the event of ethylene breakthrough, to keep the saturation of ethylene dissolved in the liquid phase of the lower zone at a given value.

Preferably, the reaction chamber also comprises a liquid level sensor; said level is kept constant by adjusting the flow rate of the effluent withdrawn in step c). Preferably, the level sensor is located at the interphase between the liquid phase and the headspace.

ii) A Means for Introducing Ethylene

According to the invention, the reaction chamber i) comprises a means for introduction of the gaseous ethylene located in the lower part of said chamber, more particularly in the lateral lower part.

Preferably, the means for introduction ii) of the ethylene is chosen from a pipe, a network of pipes, a multi-tubular distributor, a perforated plate or any other means known to a person skilled in the art.

In a specific embodiment, the means for introduction of the ethylene is located in the recirculation loop iv).

Preferably, a gas distributor, which is a device which makes it possible to disperse the gas phase uniformly over the entire liquid cross section, is positioned at the end of the introduction means ii) within the reaction chamber i). Said device comprises a network of perforated pipes, the diameter of the orifices of which is between 1.0 and 12.0 mm, preferably between 3.0 and 10.0 mm, in order to form ethylene bubbles of millimetric size in the liquid.

iii) A Means for Introducing the Catalytic System

According to the invention, the reaction chamber i) comprises a means iii) for introducing the catalytic system.

Preferably, the introduction means iii) is located on the lower part of the reaction chamber and preferably at the bottom of said chamber.

According to an alternative embodiment, the catalytic system is introduced into the recirculation loop.

The means iii) for introducing the catalytic system is chosen from any means known to a person skilled in the art and is preferably a pipe.

In the embodiment in which the catalytic system is employed in the presence of a solvent or of a mixture of solvents, said solvent is introduced by an introduction means located in the lower part of the reaction chamber, preferably at the bottom of the reaction chamber or else in the recirculation loop.

iv) A Recirculation Loop

According to the invention, the liquid phase is rendered homogeneous and also the temperature within the reaction chamber is regulated by the use of a recirculation loop comprising a means on the lower part of the reaction chamber, preferably at the bottom, for withdrawing a liquid fraction toward one or more heat exchanger(s), so enabling the cooling of said liquid, and a means for introducing said cooled liquid into the liquid phase in the upper part of the reaction chamber.

The recirculation loop can advantageously be implemented by any necessary means known to a person skilled in the art, such as a pump for the withdrawal of the liquid fraction, a means capable of regulating the flow rate of the liquid fraction withdrawn, or else a pipe for purging at least part of the liquid fraction.

Preferably, the means for withdrawing the liquid fraction from the reaction chamber is a pipe.

The heat exchanger(s) capable of cooling the liquid fraction is (are) chosen from any means known to a person skilled in the art.

The recirculation loop enables effective homogenization of the concentrations and makes it possible to control the temperature in the liquid phase within the reaction chamber.

v) A Headspace Recycle Loop

According to the invention, the device comprises a loop for recycling the gas phase into the lower part of the liquid phase. Said loop comprises a means for withdrawing a gaseous fraction in the gas phase of the reaction chamber, and a means for introducing said withdrawn gaseous fraction into the liquid phase in the lower part of the reaction chamber.

The recycle loop makes it possible, advantageously, to compensate the phenomenon of breakthrough and to prevent the pressure in the reaction chamber increasing, while keeping the saturation of ethylene dissolved in the liquid phase at a desired level.

Another advantage of the recycle loop is to improve the volume productivity of the device and therefore to reduce the costs. In one preferred embodiment, the recycle loop further comprises a compressor.

In one embodiment, the gaseous fraction withdrawn is introduced by way of the means ii) for introducing gaseous ethylene.

In another embodiment, the gaseous fraction withdrawn is introduced by way of a gas distributor, which is a device which makes it possible to disperse the gas phase uniformly over the entire liquid cross section and is positioned at the end of the introduction means within the reaction chamber i). Said device comprises a network of perforated pipes, the diameter of the orifices of which is between 1.0 and 12.0 mm, preferably between 3.0 and 10.0 mm, in order to form ethylene bubbles of millimetric size in the liquid.

Preferably, the means for introducing the gaseous fraction withdrawn is chosen from a pipe, a network of pipes, a multi-tubular distributor, a perforated plate or any other means known to a person skilled in the art.

BRIEF DESCRIPTION OF THE DRAWINGS

FIG. 2 provides a schematic illustration of one particular embodiment of the subject matter of the present invention, without limiting the scope of the invention.

EXAMPLES

The examples below illustrate the invention without limiting the scope thereof.

Figure 1:
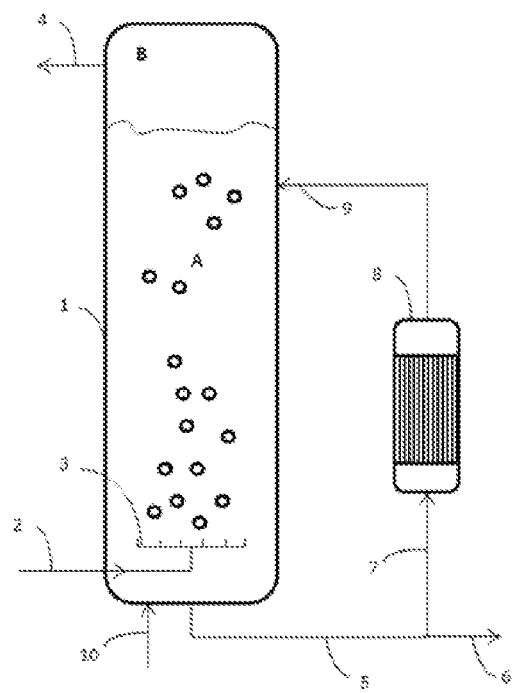
FIG. 1 illustrates a reaction device according to the prior art. This device consists of a reaction chamber (1) comprising a lower zone comprising a liquid phase A and an upper zone comprising a gas phase B, a means (2) for introducing gaseous ethylene by way of a gas distributor (3) into the liquid phase A. The gas phase B comprises a purging means (4). In the bottom of the reaction chamber (1) there is a pipe located for withdrawing a liquid fraction (5). Said fraction (5) is divided into two streams, a first, principal stream (7) which is sent to a heat exchanger (8) and then introduced by way of a pipe (9 into the liquid phase A, and a second stream (6), which corresponds to the effluent sent to a later step. The pipe (10) in the bottom of the reaction chamber enables the introduction of the catalytic system.

Example 1: Comparative Example Corresponding to FIG. 1

The ethylene oligomerization process is implemented in a bubble column reactor. The reactor is operated at a pressure of 5.0 MPa and at a temperature of 120° C. The reaction volume is composed, in accordance with the figure at 1, of two zones A and B, a column with a diameter of 2.97 m and a liquid height of 6.0 m, and a recirculation loop having a total volume of 5.0 $m^3$.

The column is equipped with a device for injecting gaseous ethylene, situated at 1.0 m from the bottom of the column.

The catalytic system introduced into the reaction chamber is a chromium-based catalytic system having a chromium content of 4.37 ppm, as described in patent FR 3 019 064, in the presence of cyclohexane as solvent.

The purge flow rate is 0.0045 kg/s.

The volumetric productivity of this reactor is 0.134 tonne of hex-1-ene produced per hour per $m^3$ of reaction volume.

The performance levels of this reactor enable a saturation of dissolved ethylene of 62.0%.

The production of hex-1-ene is 6.25 tonnes/hour, the selectivity for hex1-ene is 81.2 wt %, and the residence time in the reactor is 76 minutes, for a proportion by mass of solvent of 1.0. Said proportion of solvent is calculated as the ratio by mass of the flow rate of injected solvent to the flow rate of injected gaseous ethylene.

Example 2: According to the Invention Corresponding to FIG. 2

Figure 2:
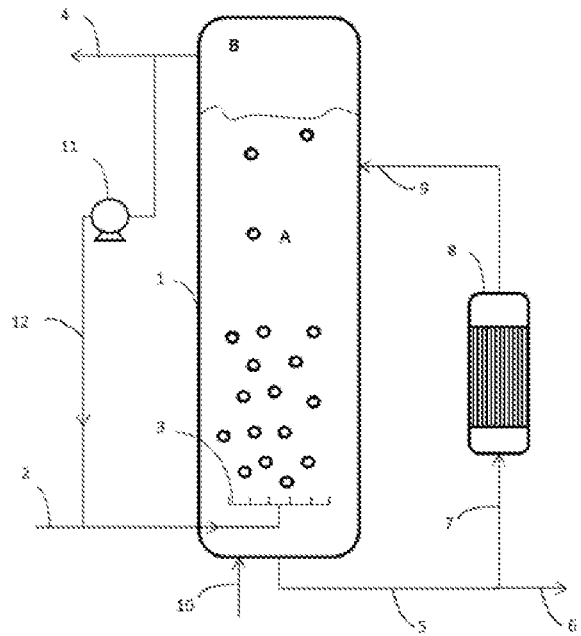
FIG. 2 illustrates a device enabling the implementation of the process according to the invention. Said device differs from the device of FIG. 1 in that a gaseous fraction of the gas phase B is sent to a compressor (11) and is recycled via a pipe (12) connected to the means (2) for introducing gaseous ethylene into the lower part of the zone A comprising the liquid phase A.

The oligomerization process according to the invention is implemented in a device having dimensions identical to the device employed in example 1, further comprising, in accordance with the invention, a loop for recycling the headspace into the liquid phase, as described in FIG. 2. The ethylene oligomerization process is implemented in a bubble column reactor. The reactor is operated at a pressure of 5.0 MPa and at a temperature of 120° C.

The catalytic system introduced into the reaction chamber is a chromium-based catalytic system having a chromium content of 4.38 ppm, as described in patent FR 3 019 064, in the presence of cyclohexane as solvent.

The volumetric productivity of this reactor is 0.194 tonne of hex-1-ene produced per hour per $m^3$ of reaction volume.

The performance levels of the oligomerization process according to the invention enable a saturation of dissolved ethylene of 90.0%.

The production of hex-1-ene is 9.06 tonnes/hour, the selectivity for hex-1-ene is 83.3 wt %, and the residence time in the reactor is 52.5 minutes, for a proportion by mass of solvent of 1.0. Said proportion of solvent is calculated as the ratio by mass of the flow rate of injected solvent to the flow rate of injected gaseous ethylene.

The process according to the invention therefore clearly allows an increase in the ethylene saturation in the liquid phase, so enabling an improvement in the productivity of the oligomerization process, with a smaller residence time and a better selectivity for hex-1-ene.

The invention claimed is:

1. An oligomerization process implemented in a gas/liquid in a reaction chamber at a pressure of between 0.1 and 10.0 MPa, at a temperature of between 30 and 200° C., comprising the following steps:
   a) a step of introducing a catalytic oligomerization system comprising a metal catalyst and an activating agent into the reaction chamber comprising a liquid phase in a lower zone and a gas phase in an upper zone,
   b) a step of contacting said catalytic oligomerization system with gaseous ethylene by introducing said ethylene into the lower zone of the reaction chamber,
   c) a step of withdrawing a liquid fraction from the liquid phase,
   d) a step of cooling the liquid fraction withdrawn in step c) by passing said fraction into a heat exchanger,
   e) a step of introducing the fraction cooled in step d) into the upper part of the lower zone of the reaction chamber, and
   f) a step of recycling a gaseous fraction withdrawn from the upper zone of the reaction chamber and introduced at the lower part of the reaction chamber into the liquid phase.

2. Process according to claim 1, wherein the liquid phase in the lower zone of the reaction chamber has a degree of saturation in dissolved ethylene of more than 70.0%.

3. Process according to claim 1, wherein the gas phase withdrawn in step f) is introduced as a mixture with the gaseous ethylene introduced in step b).

4. Process according to claim 1, wherein the rate of withdrawal of the gaseous fraction in step f) is between 0.1 and 100% of the flow rate of gaseous ethylene introduced in step b).

5. Process according to claim 1, wherein the gaseous fraction withdrawn in step f) is introduced at the lateral lower part of the reaction chamber.

6. Process according to claim 1, wherein the rate of withdrawal of the gaseous fraction in step f) is dependent on the pressure within the reaction chamber.

7. Process according to claim 1, wherein a second gaseous purge stream is withdrawn from the gas phase.

8. Process according to claim 7, wherein the flow rate of the second gaseous stream is between 0.005 and 1.00% of the flow rate of ethylene introduced in step b).

9. Process according to claim 1, wherein a gaseous hydrogen stream is introduced in step b) into the reaction chamber, with a flow rate representing 0.2 to 1.0% by mass of the flow rate of ethylene.

10. Process according to claim 1, wherein the concentration of the metal catalyst in the catalytic oligomerization system is between 0.1 and 50.0 ppm by mass of atomic metal relative to the reaction mass.

11. Process according to claim 1, wherein the catalytic oligomerization process is implemented continuously.

12. Process according to claim 1, wherein linear olefins comprising 4 to 20 carbon atoms are obtained.

13. A reaction device for implementing the process according to claim 1 comprising:
   the reaction chamber i), of elongate shape along the vertical axis, comprising
      the liquid phase located in the lower zone and comprising reaction products, gaseous and dissolved ethylene, the catalytic oligomerization system and an optional solvent, and
      the gas phase located in the upper zone above the lower zone and comprising gaseous ethylene,
   a means ii) for introducing gaseous ethylene, located in the lateral lower part of said reaction chamber, employing a means for distributing the gaseous ethylene within said liquid phase of the reaction chamber,
   a means iii) for introducing the catalytic oligomerization system, comprising the metal catalyst, the activating agent and at least one additive, said means being located in the lower part of the reaction chamber,
   a recirculation loop iv) comprising a withdrawing means at the base, optionally at the bottom, of the reaction chamber for withdrawing the liquid fraction toward the heat exchanger for cooling of said liquid fraction, and a means for introducing said cooled liquid fraction, said introducing being carried out into the liquid phase in the upper part of the lower zone of the reaction chamber, and
   a recycle loop v) for the gas phase into the lower zone of the liquid phase, comprising a means for withdrawing the gaseous fraction at the gas phase of the reaction chamber and a means for introducing said withdrawn gaseous fraction into the liquid phase in the lower zone of the reaction chamber.

14. Device according to claim 13, wherein the withdrawn gaseous fraction is introduced by way of the means ii) for introducing gaseous ethylene.

15. Device according to claim 13, wherein the gaseous fraction withdrawn in the recycle loop is introduced by way of a gas distributor.

* * * * *